United States Patent [19]
Roche et al.

[11] Patent Number: 5,817,340
[45] Date of Patent: Oct. 6, 1998

[54] PHARMACEUTICAL COMPOSITIONS CONTAINING FAMOTIDINE AND ALUMINUM HYDROXIDE OR MAGNESIUM HYDROXIDE

[75] Inventors: Edward John Roche, Paoli, Pa.; Susan Decoteau, Mystic, Conn.; Eleanor Freeman, Norristown, Pa.

[73] Assignee: McNeil-PPC, Inc., Skillman, N.J.

[21] Appl. No.: 756,080

[22] Filed: Nov. 25, 1996

Related U.S. Application Data

[63] Continuation of Ser. No. 264,223, Jun. 22, 1994, abandoned, which is a continuation of Ser. No. 983,923, Dec. 1, 1992, abandoned.

[51] Int. Cl.[6] .............................. A61K 9/26; A61K 9/16; A61K 9/50
[52] U.S. Cl. .......................... 424/470; 424/490; 424/455; 424/472; 424/473; 424/464; 424/687; 424/690; 424/692; 424/493; 424/494; 424/495; 424/497; 424/498; 514/370
[58] Field of Search ..................... 424/464, 472, 424/473, 455, 687, 690, 692, 470, 490, 493, 494, 495, 497, 498; 514/370

[56] References Cited

U.S. PATENT DOCUMENTS

| | | | |
|---|---|---|---|
| 3,048,526 | 8/1962 | Boswell | 167/82 |
| 3,922,338 | 11/1975 | Estevenel et al. | 424/41 |
| 4,198,390 | 4/1980 | Rider | 424/21 |
| 4,283,408 | 8/1981 | Hirata et al. | 424/270 |
| 5,075,114 | 12/1991 | Roche | 424/470 |
| 5,213,808 | 5/1993 | Bar-Shalom et al. | 424/473 |
| 5,229,137 | 7/1993 | Wolfe | 424/687 |
| 5,260,072 | 11/1993 | Roche et al. | 424/464 |

FOREIGN PATENT DOCUMENTS

| | | |
|---|---|---|
| 0 294 933 A3 | 4/1988 | European Pat. Off. . |
| 0286781 A2 | 10/1988 | European Pat. Off. . |
| 0 290 229 B1 | 7/1991 | European Pat. Off. . |
| WO 92/00102 | 6/1991 | WIPO . |

OTHER PUBLICATIONS

"The Dating Game", text of speech given at The Proprietary Assn.'s Twelfth Manufacturing Controls Seminar, Cherry Hill, NJ. Oct. 5–6, 1978 by Joel S. Davis, Chief, Prod. Quality Branch, FDA, pp. 1–15.

Physician's Desk Reference, 45th ed., Medical Economics Co., Oradell, NJ, pp. 1478–1479 (1991).

"Organic Chemistry," Morrison et al., Allyn and Bacon, Inc., Boston, 1973, pp. 55–58.

*Primary Examiner*—Marianne M. Cintins
*Assistant Examiner*—M. Moezie
*Attorney, Agent, or Firm*—Joseph F. Leightner; Hal Brent Woodrow

[57] ABSTRACT

A solid oral dosage form for the treatment of gastrointestinal disorders comprising a therapeutically effective amount of a therapeutically effective amount of guanidinothiazole compound; and a therapeutically effective amount of an antacid wherein the pharmaceutical and an antacid are separated by a barrier which is substantially impermeable to an antacid.

7 Claims, 6 Drawing Sheets

PHARMACEUTICAL COMPOSITIONS CONTAINING FAMOTIDINE AND ALUMINUM HYDROXIDE OR MAGNESIUM HYDROXIDE

This is a continuation of application Ser. No. 08/264,223, filed Jun. 22, 1994, now abandoned which is a continuation application of application Ser. No. 07/983,923, filed Dec. 1, 1992, now abandoned.

FIELD OF INVENTION

This invention relates to a solid oral dosage form for a pharmaceutical composition for treating gastrointestinal distress comprising a therapeutically effective amount of an antacid and a therapeutically effective amount of a guanidinothiazole compound. This inventions also relates to methods of making the aforesaid solid oral dosage form.

BACKGROUND OF THE INVENTION

An antacid have been utilized in combination with a variety of therapeutic compounds. One combination which is believed to be particularly advantageous is the combination of antacids with $H_2$ blockers (such as guanidinothiazole compounds) to provide enhanced relief for gastrointestinal distress. However, in formulating antacid with these guanidinothiazole compounds ($H_2$ blockers), we have discovered that without special precautions being taken, that the guanidinothiazole compounds are degraded in the presence of antacids.

SUMMARY OF THE INVENTION

In accordance with the present invention, we have discovered a solid oral dosage form for the treatment of gastrointestinal disorders comprising a therapeutically effective amount of a guanidinothiazole compound suitable for the treatment of gastric disorders and pharmacologically acceptable acid addition salts thereof; and a therapeutically effective amount of an antacid wherein the oral dosage form has a first portion containing the antacid and a second portion containing the guanidinothiazole compound suitable for the treatment of gastric disorders wherein the first and second portions are in contact with and separated by a barrier which is substantially impermeable to the antacid.

In an another embodiment of the present invention, we have further discovered a solid oral dosage form for the treatment of gastrointestinal disorders comprising a therapeutically effective amount of a guanidinothiazole compound suitable for the treatment of gastric disorders and pharmacologically acceptable acid addition salts thereof, wherein the guanidinothiazole compound suitable for the treatment of gastric disorders is provided in the form of coated granules which are coated with a coating impermeable to an antacid; a therapeutically effective amount of an antacid; and pharmaceutically acceptable excipients.

In a further embodiment of the invention, we have discovered a method for manufacturing a multilayered solid dosage form having one layer containing at least one antacid and one layer containing a guanidinothiazole compound suitable for treating gastric disorders with a barrier sandwiched between the two layers comprising pressing one of two granulations each containing pharmaceutically acceptable excipients with either a therapeutic amount of an antacid or a therapeutic amount of a guanidinothiazole compound suitable for the treatment of a gastric disorder therein, to form a first layer with one exposed surface, then applying to the exposed surface a material which is substantially impermeable to an antacid to form a coated layer with a coated surface; contacting the coated surface with the remaining granulation; then pressing the granulation and coated layer to form a multilayered solid oral dosage form wherein the antacid and the guanidinothiazole compound are separated by the material substantially impermeable to the antacid.

In an additional embodiment of the invention, we have also discovered a method for manufacturing a solid oral dosage form comprising forming granules containing a guanidinothiazole compound suitable for the treatment of gastric disorders, coating the granules with a coating impermeable to an antacid to form coated guanidinothiazole granules, mixing a therapeutically effective amount of an antacid with a therapeutically effective amount of coated guanidinothiazole granules and pharmaceutically acceptable excipients to form a compression mixture, then pressing the compression mixture to form a solid oral dosage form.

Other aspects, objects and several advantages of this invention will be apparent from the foregoing specification and claims.

DETAILED DESCRIPTION

Figure 1:
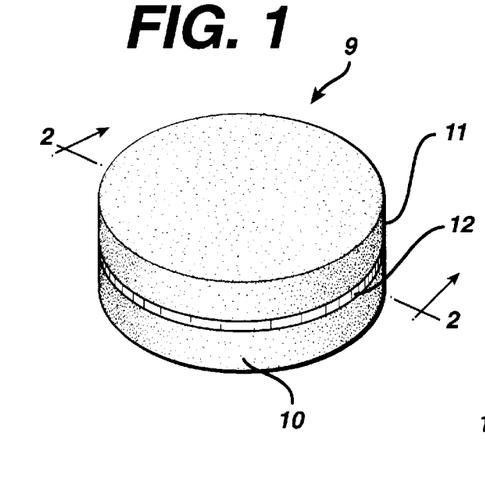
FIG. 1 is a perspective view of a pharmaceutical tablet in accordance with one embodiment of the present invention.
Figure 2:
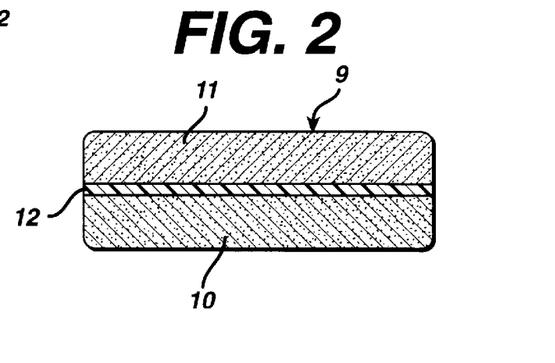
FIG. 2 is a sectional view of an embodiment of the present invention.

Referring to FIGS. 1 and 2, indicated generally as 9 is a tablet constructed in accordance with one of the embodiments of the invention. Tablet 9 comprises a first portion or layer 10 containing at least one antacid and a second portion or layer 11 containing a guanidinothiazole compound with each of the first and second layers 10, and 11 being separate and discrete from the other layer. Sandwiched between layers 10 and 11 is a barrier 12 which may be a film or diaphragm or membrane composed of plastic material. Alternatively barrier 12 could also be formed of a compressed pharmaceutically acceptable excipient inert to both the antacid(s) and the guanidinothiazole compound. The pharmaceutical excipient could be formed by compressing the excipient as a middle layer in a multiple layered tablet. Barrier 12 maintains the antacid in first layer 10 out of contact with the guanidinothiazole compound for the treatment of gastric disorders in second layer 11 and prevents migration of the antacid from layer 10 to layer 11 as well as preventing migration of the guanidinothiazole compounds for the treatment of gastric disorders from layer 11 to layer 10.

Figure 3:
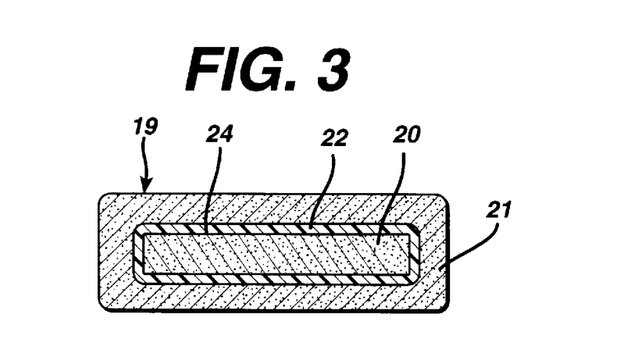
FIG. 3 is a sectional view of another embodiment of the present invention.

Referring to FIG. 3, in this embodiment 19, the first portion containing the antacid is in the form of an inner core 20, and the second portion comprising the guanidinothiazole compound in the form of an outer layer 21 encompassing inner core 20. Barrier 22 is disposed between inner core 20 and outer layer 21 and encompasses inner core 20. Outer layer 21 encompasses barrier 22. Barrier 22 may be in the form of a thin plastic film or sheet surrounding and enclosing inner core 20, or barrier 22 may be in the form of a thin plastic film applied as a coating on the outer surface 24 of inner core 20 before outer layer 21 is formed.

In the embodiments of FIGS. 2 and 3, the portions 10 and 20, containing the antacid, are each a mixture of ingredients comprising an antacid and a solid, inert filler or carrier or other antacid adsorbing material.

Figure 4:
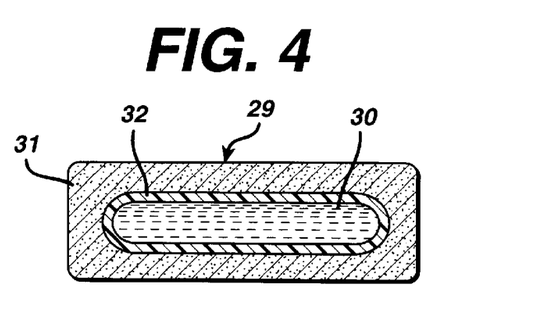
FIG. 4 is a sectional view of a third embodiment of the present invention.

Referring to FIG. 4, in this embodiment 29, the first portion comprising the antacid is in the form of an inner core 30 which may consist entirely of an antacid or the antacid provided in a viscous liquid condition. The outer core comprising the guanidinothiazole compound 31 may be similar to the outer core 21 in the embodiment of FIG. 3. The inner core of an antacid is encompassed by and contained within a barrier 32 which may be in the form of a container for a liquid antacid, e.g. a soft, chewable gelatin capsule shell. As an alternative to providing the antacid within container 21 in a viscous liquid condition, the antacid may be provided as part of a solid mixture, as is the case with both the antacid-containing layer 10 in the embodiment 9 of FIG. 2 and the antacid-containing inner core 20 in the embodiment 10 of FIG. 3.

In all of the above-described embodiments, the antacid is separate from the matrix formed by the guanidinothiazole compound in its respective portion (11, 21 or 31), and the an antacid remains substantially separated from the matrix during an extended shelf life because the barrier (12, 22, 32) prevents the antacid from contacting the guanidinothiazole compound. The antacid will be considered substantially separate from the guanidinothiazole compound if the barrier prevents the antacid from degrading more than an additional 1% by weight of the guanidinothiazole compound as compared to an identically formulated solid dosage form not containing an antacid for at least 3 months at ambient temperature and humidity. Preferably less than 1 percent by weight of the famotidine contained in the dosage form will be degraded after 6 months from the manufacturing of the solid dosage form.

The barrier 12 or 22 may be composed of a pharmaceutically acceptable film forming polymer which is physiologically inert and prevents the therapeutic ingredients in the separate portions of the solid dosage form from contacting. Suitable pharmaceutically acceptable polymers may be selected from the group consisting of cellulose derivatives, polyvinyl pyrrolidone (containing little or no polymerization initiator), polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of acrylic acid and tertiary amino alkyl methacrylate, copolymers of methacrylate and tertiary amino alkyl methacrylate, copolymers of ethylacrylate methyl methacrylate and quaternary amino alkyl methacrylate and combinations of two or more thereof. Cellulose derivatives includes pharmaceutically acceptable cellulose derivatives selected from the group consisting of methyl cellulose, hydroxypropyl methylcellulose, ethyl cellulose, hydroxyethyl cellulose, hydroxypropyl cellulose, carboxymethyl cellulose, cellulose acetate butyrate, cellulose acetate phthalate, hydroxypropyl methylcellulose phthalate, hydroxypropyl methylcellulose acetate succinate and combinations of two or more thereof. The acrylic acid and methacrylic acid copolymers listed above also includes copolymers of sodium and potassium salt thereof. A suitable ester copolymer of methacrylic and tertiary amino alkyl methacrylate is dimethylaminoethyl methacrylate-methacrylate.

The antacid used in the present invention can be administered in dosage range of from about 5 ANC to about 160 ANC per dosage unit, preferably from 5 ANC to 20 ANC wherein the daily dosage does not exceed 160 ANC (ANC is determined according to the Federal Register 39-19862, Jun. 4th 1974). The dosage ranges may vary for age and weight of a patient as well as the severity of symptoms.

Suitable antacids for the practice of this invention may be selected from the group consisting of antacids acceptable to the Food & Drug Administration, including but not limited to aluminum carbonate, aluminum hydroxide (or as aluminum hydroxide-hexitol stabilized polymer, aluminum hydroxide-magnesium hydroxide codried gel, aluminum hydroxide-magnesium trisilicate codried gel, aluminum hydroxide-sucrose power hydrated), aluminum phosphate, aluminum hydroxy carbonate, dihydroxy aluminum sodium carbonate, aluminum magnesium glycinate, dihydroxy aluminum aminoacetate, dihydroxyaluminum aminoacetic aid, bismuth aluminate bismuth carbonate, bismuth subcarbonate, bismuth subgallate, bismuth subnitrate, calcium carbonate, calcium phosphate, hydrated magnesium aluminate activated sulfate, magnesium aluminate, magnesium aluminosilicates, magnesium carbonate, magnesium glycinate, magnesium hydroxide, magnesium oxide, magnesium trisilicate, sodium bicarbonate and combinations of two or more thereof.

Preferred antacids include antacids selected from the group consisting of aluminum hydroxide, magnesium carbonate, calcium carbonate, magnesium hydroxide and mixtures of two or more thereof. Preferred mixtures are mixtures of aluminum hydroxide and calcium carbonate, and calcium carbonate and magnesium hydroxide, wherein the antacids provide in an amount sufficient to provide at least 5 ANC and preferably from 5 to 20 ANC.

Suitable guanidinothiazole compounds for use in this invention are described in U.S. Pat. No. 4,283,408 which is hereby incorporated by reference herein. These compounds are histamine $H_2$-receptor antagonists. A 2 preferred group of guanidinothiazole compounds are of the formula:

wherein R represents a hydrogen atom or a lower alkyl group; $R_1$ represents an amino group, a mono- or di-lower alkylamino group, an arylamino group or an aralkylamino group; $R_2$ represents a hydrogen atom, a lower alkyl group, a lower alkenyl group or a lower alkynyl group; Y represents a sulfur atom or a methylene group; m and n each represent an integer of 1–3. The term "lower" in the above definition means a straight or branched carbon chain having 1–5 carbon atoms. The preferred guanidinothiazole compound is famotidine. A complete discussion of the use and synthesis of guanidinothiazole compound may be found in U.S. Pat. No. 4,283,408.

The amount of guanidinothiazole compound suitable for the treatment of gastric disorder in combination with an antacid(s) should be sufficient to provide a therapeutic dosage to a patient to inhibit the secretion of gastric acid in the treatment of gastric ulcers and duodenal ulcers. The effective amount of guanidinothiazole compound in a combination dosage with effective amounts of an antacid vary from patient to patient depending on the patient's condition, the particular antacid selected, but will generally vary from about 20 mg to about 800 mg per day (which may be conveniently administered in 1 to 4 doses). The preferred dosage ranges for famotidine in combination with an antacid is in the range of from about 5 mg to about 20 mg of famotidine per dose and preferably 10 mg of famotidine per dose. The preferred daily dosage of famotidine is about 20 mg for a 70 kg adult. A preferred adult dose of famotidine and antacid given for the treatment of gastrointestinal distress is 10 mg of famotidine with a sufficient amount of at least one antacid to provide in the range of from about 5 to about 10 ANC. A preferred weight ratio of famotidine to an antacid is in the range of from about 1 to 75 to about 1 to 10.

Excipient suitable for use in either single layer or bilayer solid dosage forms include fillers, binders, sweeteners, artificial sweeteners, lubricants, glidants, disintegrants, colors, adsorbents, acidifying agents and flavoring agents. The choice of excipient will depend on the solid oral dosage form desired (i.e. tablets, pills or capsule) and whether the dosage is to be chewable or swallowed whole. The following non-limiting list of excipients provides the illustrate excipients that could be used in a chewable solid oral dosage form:
a) an effective amount of a sweetener selected from the group consisting of mannitol, dextrose, fructose, sorbitol, sucrose and lactose;
b) an effective amount of a binder selected from the group consisting of microcrystalline cellulose, alginic acid, acacia acid, carboxymethyl cellulose and hydroxypropyl cellulose;
c) an effective amount of an artificial sweetener selected from the group consisting of asparatame, sucralose and saccharin;
d) an effective amount of a lubricant selected from the group consisting of magnesium stearate, talc, stearic acid, calcium stearate, zinc stearate, stearic acid, hydrogenated vegetable oil, leucine, glycerides, and sodium stearyl fumarate; and
e) an effective amount of an acidifying agent selected from the group consisting of citric acid and malic acid;
f) an effective amount of flavoring agent selected from the group consisting of artificial and natural flavors; and
g) an effective amount of a filler selected from the group consisting of dibasic calcium phosphate dihydrate and monobasic calcium phosphate monohydrate.

Additionally, the components listed above (without the sweeteners and flavorants) could be used in swallowable tablets or caplets. For the formulation of a swallowable caplets or tablets it may be desirable to incorporate an effective amount of a disintegrant such as disintegrants selected from the group consisting of carboxymethyl cellulose, alkali salts of carboxymethyl cellulose (such as sodium and calcium salts), sodium cellulose glycolate, sodium carmellose glycolate, sodium carboxymethyl starch, sodium starch glycolate, and alkali salts of carmellose (such as sodium and calcium salts).

Other suitable excipients can be found in the *Handbook of Pharmaceutical Excipients,* published by the American Pharmaceutical Association which is incorporated herein by reference. The following formulation provides weight percentages (based on the total weight of each layer being 100 weight percent) of the various components of a chewable multilayered tablet:

| Antacid Layer | |
|---|---|
| Granulated Antacid(s) | 35% to 75% |
| Excipients | |
| Filler | 0% to 45% |
| Binders | 0% to 10% |
| Sweetener | 8% to 50% |
| Artificial Sweetener | 6% to 8% |
| Lubricant | 0.25% to 5.0% |
| Flavoring Agent | 0.01% to 0.03% |
| Famotidine Layer | |
| Famotidine* | 1% to 20% |
| Excipient | |
| Filler | 0% to 70% |
| Binder | 0% to 10% |
| Sweetener | 10% to 80% |
| Artificial Sweetener | 0.5% to 3% |
| Lubricant | 0.25% to 5% |
| Flavoring Agent | 0.01% to 0.03% |
| Barrier** | 4% to 20% |

*The amount of Famotidine listed above is for the amount of active Famotidine only.
**The amount of barrier material is based on the total weight of the solid dosage form equalling 100 weight percent.

Those skilled in the art will readily recognize that the total weight of the solid dosage form can be varied to provide conveniently swallowable pill or caplet provided in larger sizes suitable for use as a solid chewable dosage form. It is currently preferred that the weight ratio of the antacid layer to the famotidine layer be in the range of from about 2:1 to about 4:1.

Suitable methods for manufacturing single and multilayered solid dosage forms are known in the art. Two sources for these techniques are *Remington's Pharmaceutical Sciences,* 18th Edition published by Mack Publishing Company and the three volume series *Pharmaceutical Dosage Forms: Tablets,* Volumes 1–3, 2nd edition, edited by Herbert A. Lieberman, Leon Lachman and Joseph B. Schwartz, published by Marcel Dekker which are hereby incorporated by reference herein.

The method for manufacturing the multilayered solid dosage form having one layer containing an antacid and one layer containing a pharmaceutical suitable for treating gastric disorders with a barrier sandwiched between the two layers comprises pressing one of two granulations each containing pharmaceutically acceptable excipients with either a therapeutic amount of an antacid or a therapeutic amount of a guanidinothiazole compound therein, to form a first layer with one exposed surface, then coating the exposed surface with a material which is substantially impermeable to an antacid to form a coated layer with coated surface, then contacting the coated surface with the remaining granulation, and then pressing the granulation and coated layer to form a multilayered solid oral dosage form wherein the antacid and the guanidinothiazole compound are separated by the material substantially impermeable to an antacid. The first layer formed in this process is generally a soft layer to allow the barrier to be put in place and provide an even appearance to the interface between the layers. The barrier may be applied as a granulation to be pressed into a layer or spray coated on the surface which will sandwich the barrier. The coatings suitable for spray coating granules of pharmaceuticals are also suitable for use as a sprayed on barrier layer.

In an alternate embodiment of the present invention may be provided in the form of a coated granule. These granules may be formed by granulating the pharmaceutical with suitable granulation excipients in a conventional granulation process such as a wet granulation or rotogranulation. The granules produced by these processes are preferably spherical in shape with a particle size from about 125 microns to about 500 microns for swallowable solid dosage forms and a particle range of from about 150 microns to about 300 microns for chewable (to avoid a gritty texture).

After the granulation, the granules will be coated by a conventional coating process such as roto-coating (coating in a rotogranulator), Wurster coating or fluid bed particle coating. The coatings material for the granules of the pharmaceutical suitable for treating gastric disorders should be composed of a pharmaceutically acceptable film forming polymer which is physiologically inert, prevents the antacid from penetrating or coating the coated granule. Suitable coating material are pharmaceutically acceptable film forming polymers and combinations thereof. Suitable coatings are provided in the following Table:

| Polymer System | Coat Level | Polymer Ratio |
| --- | --- | --- |
| Cellulose Acetate/PVP | 8–18% | 90/10 to 60/40 |
| Cellulose Acetate Butyrate/PVP | 8–18% | 90/10 to 60/40 |
| Cellulose Acetate/HPC | 8–18% | 90/10 to 50/50 |
| Cellulose Acetate Butyrate/HPC | 8–18% | 90/10 to 50/50 |
| Cellulose Acetate/ methacrylic acid copolymers (Eudragit E 100) | 8–18% | All ratios |
| Cellulose Acetate Butyrate/ Eudragit E 100 | 8–18% | All ratios |
| Ethyl Cellulose/PVP | 8–18% | 90/10 to 60/40 |
| Ethyl Cellulose/HPC | 8–18% | 90/10 to 50/50 |
| Ethyl Cellulose/Eudragit E 100 | 8–18% | All ratios |
| HPC | 10–20% | NA |
| HEC | 10–20% | NA |
| Eudragit E 100 | 10–20% | NA |
| HPMC | 10–20% | NA |
| HEC/HPMC | 10–20% | All ratios |
| HPC/HPMC | 10–20% | All ratios |
| HEC/HPC | 10–20% | All ratios |
| VPS | 10–20% | NA |
| CA/2-VPS | 8–18% | All ratios |
| CAB/2-VPS | 8–18% | All ratios |
| Ethyl Cellulose/2-VPS | 8–18% | All ratios |
| Cellulose Triacetate/PVP | 8–18% | 90/10 to 60/40 |
| Cellulose Triacetate/HPC | 8–18% | 90/10 to 50/50 |
| Cellulose Triacetate/ Eudragit E 100 | 8–18% | All ratios |

PVP - polyvinylpyrrolidone
HPC - Hydroxypropyl cellulose
HEC - Hydroxyethyl cellulose
HPMC - Hydroxypropylmethyl cellulose
CA - Cellulose Acetate
CAB - Cellulose Acetate Butyrate
Eudragit E 100 - Methylacrylic acid copolymers
VPS - 2-vinyl pyridine styrene co-polymer The preferred coatings are cellulose acetate, cellulose triacetate and cellulose acetate butyrate with polyvinyl pyrrolidone, methylaminoethyl-methacrylate and neutral methacrylic acid esters (Eudragit E-100), copolymers of 2-vinylpyridine and styrene and hydroxypropylcellulose. Particularly preferred grades of polymers are cellulose acetate 320-S, 398-10, 437-75S; cellulose acetate butyrate 171, 381 and 500 (both of cellulose acetate and cellulose acetate butyrate are available from FMC and fully described in *Cellulose Esters: Polymers for Drug Delivery* published in 1986; Povidone K29/32 and K90 (which is fully described in the USP); Klucel EF, LF, and JF (HPC having an average molecular weight of from about 60,000 to about 125,000); Methocel E5 and E15; Natrosol 250L; and Ethocel N10. The amount of coating applied on as a weight percentage of the coated granules weight will vary with the coating process coating granulation and granules used. The appropriate amount of coating can be determined by determining dissolution of the active pharmaceutical suitable for the treatment of gastric disorders with various coating thicknesses following the dissolution tests set forth in *The United States Pharmacopeia XXII.* As a general rule will vary from about 8% to about 20% based on the weight of the coated granule. In one preferred embodiment of the present invention granules formed by a wet rotogranulation process would be roto-coated with from about 8% to about 18% weight percent of a polymer blend of cellulose acetate and methylaminoethyl-methacrylate and neutral methacrylic acid ester.

A preferred granulation process for famotidine is to granulate famotidine with a granulation excipient selected from the group consisting of sugars (such as lactose, confectioners sugar or mannitol), microcrystalline cellulose, and cellulose.

The weight percentages of the components of this granulation process are as follows:

| | |
|---|---|
| Famotidine USP | 8%–16% |
| Granulation Excipient | 76.5%–84% |
| Coating | 8%–20% |

In a preferred embodiment of the present invention the oral solid dosage form will contain an effective amount of an antacid and an effective amount of a guanidinothiazole compound and at least one excipient wherein the pharmaceutical is provided in the form of coated granules which are coated with a coating impermeable to an antacid. This dosage form may be a tablet, multilayered tablet, pill, gelcap or capsule but will preferably be provided a chewable tablet. The coating for the granules of the pharmaceutical and the excipients are the same as previously discussed above. The following formulation provides weight percentage ranges (based on the total weight percent equalling 100 weight percent) of the various components of a chewable tablet.

| | |
|---|---|
| Granulated Antacid | 35% to 70% |
| Coated Granules of Famotidine | 2% to 8% |
| Excipients | |
| Filler | 0% to 55% |
| Binders | 0% to 20% |
| Sweetener | 0% to 65% |
| Artificial Sweetener | 0% to 10% |
| Lubricant | 0.25% to 6.0% |
| Flavoring Agent | 0.25% to 2.0% |

In a further embodiment of the present invention the coated granules of the pharmaceutical can be used in the multilayered solid dosage form previously described.

The following examples are provided to further illustrate the present invention.

MATERIALS AND METHODS

EXAMPLE I

A. Materials

The following per unit dosage blend weights were chosen simulating the antacid dosages found in commercial antacid preparations. The blends that are listed in Table 1:

TABLE 1

| | | |
|---|---|---|
| A: | Aluminum hydroxide | 200 mg |
| | Famotidine | 10 mg |
| B: | Magnesium hydroxide | 200 mg |
| | Famotidine | 10 mg |
| C: | *Aluminum hydroxide/ Magnesium hydroxide blend | 400 mg |
| | Famotidine | 10 mg |
| D: | **Calcium carbonate | 500 mg |
| | Famotidine | 10 mg |

*This blend of antacid is co-spray-dried with sorbitol and mannitol.
**The calcium carbonate was granulated with acacia gum.

The above blends were weighed to the nearest 0.10 mg. The blends were then mixed for 15 minutes in a small (16 oz) plexiglass V-blender. Before the components were blended a very small amount of magnesium stearate was dusted into the blender to facilitate the blending. The blends were stored in plastic bags at 15° C. prior to tablet compression.

B. Sample preparation

The tabletting was done manually on a single punch CARVER press. The hydraulic jack pressure was set to 4000–4500 psi. The pressing time was between 4–6 sec. To lubricate the dies, the dies were lightly dusted with magnesium stearate prior to tablet compression. Different sized dies were picked for each blend to help distinguish the tablets.

Samples of both tablets and "loose blends" were placed in open glass petri dishes (approx. 4 inch diameter). Duplicate series of samples were then placed on each of two trays. One tray was placed in a chamber maintained at 40° C. and 75% relative humidity. The other tray was placed in a chamber maintained at room temperature. Tablets were removed from the dishes with "tweezers" placed on the waxed weigh paper, and then crushed with a mortar, taking care to keep all of the tablet and its "shattered" fragments on the weighing paper.

C. Analytical Methods

The column used was a C 18$\mu$ BONDapak (brand name) with dimensions of 150 mm×4.6 mm i.d. and 5 micron particle size. A column heater was used, with the temperature set at 40° C.

The mobile phase was made to contain the final concentration in w/v % of:

1.36% sodium acetate tri-hydrate (certified A.C.S.)
7.00% Acetonitrile
91.64% deionized water This is equivalent to 7.00% acetonitrile in 0.1 Molar sodium acetate solution.

The pH of the water/sodium acetate solution was adjusted in process to pH 6.0 with acetic acid. The final pH of the mobile phase was 6.1 (±0.3).

The detection of degradation products was determined by ultraviolet absorption at 270 nm. The detector was a WATERS brand, model #481. Injection volumes of samples were 50 $\mu$L.

The pump driving the mobile phase was a WATERS brand model #510. The flow rate was 1.5 milliters per minute during the runs. For day 8 and day 15, run times for each injection were set for 8 minutes. Because of the 8 minute run times, the A3 degradate was not able to be detected; this proved to be disadvantageous because interest arose later in the A3 data. Later run times were then extended to 12 minutes to examine the A3 degradate.

Date files, chromatograms, and area under the curve detection were done via the CALS/Peak Pro link to the detector (Computerized Automated Lab Systems). This proved to be useful since baselines can be adjusted and areas under all curves can be automatically calculated. However, the amount of degradate must be calculated by hand using the peak height which can be obtained as an output of the CALS/Peak Pro program. The peak height was determined based on the ratio of a 1% famotidine standard to the degradate peak of interest.

Figure 5:
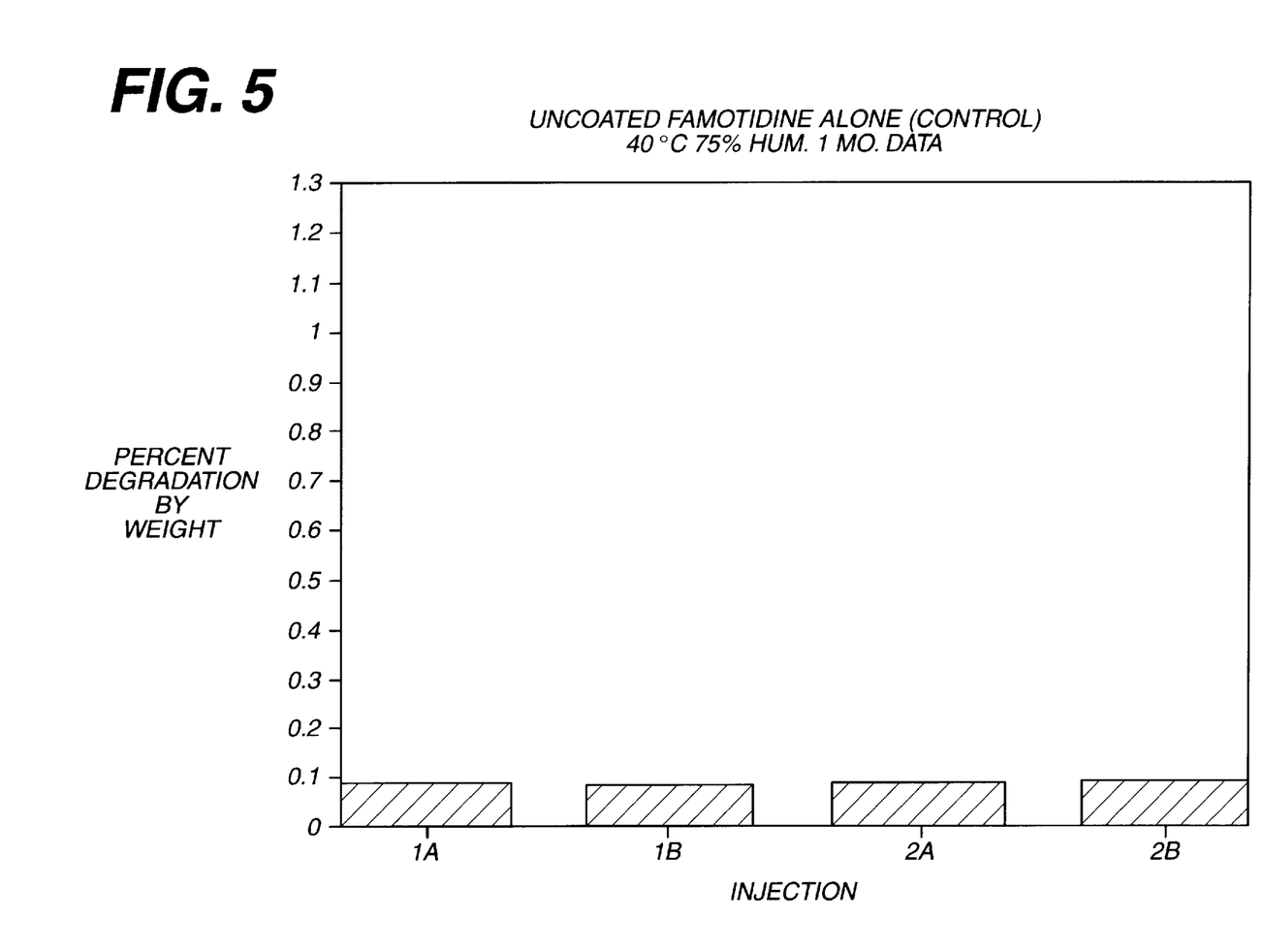
FIG. 5 provides a graphical presentation of the data from a stability test on powdered famotidine with no antacid present. The data demonstrates that famotidine is relatively stable in the absence of an antacid after being stored for one month at 40° C. in 75% relative humidity. The procedure used for the stability test is set forth in Example I.
Figure 6:
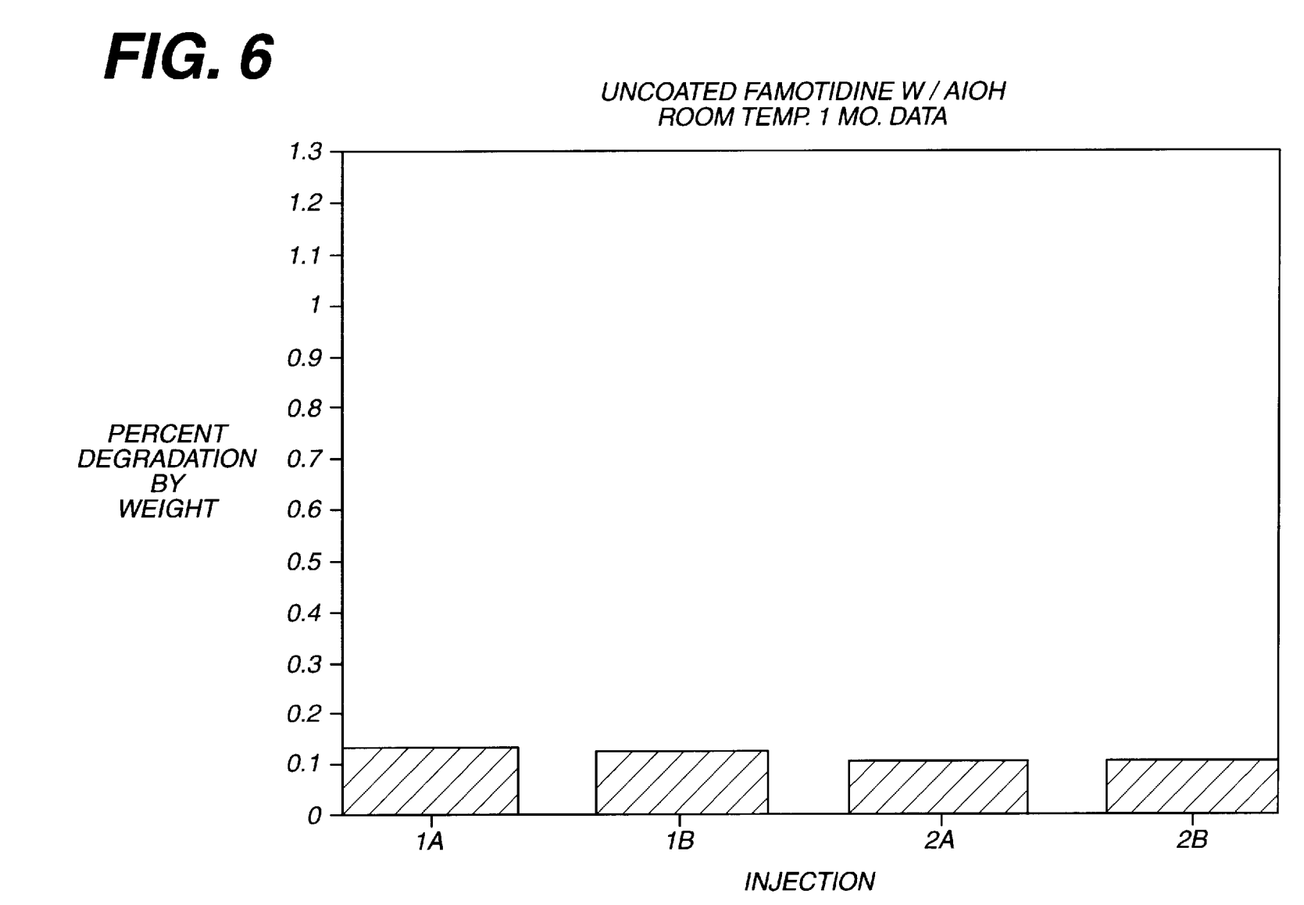
FIG. 6 provides a graphical presentation of the data from a stability test on a powdered admixture of an antacid (aluminum hydroxide) and famotidine. The data was obtained from two separate samples which were each injected twice into a column. The data demonstrates the degradation of famotidine in the presence of an antacid after being stored for one month at room temperature. The procedure used for the stability test is set forth in Example I.
Figure 7:
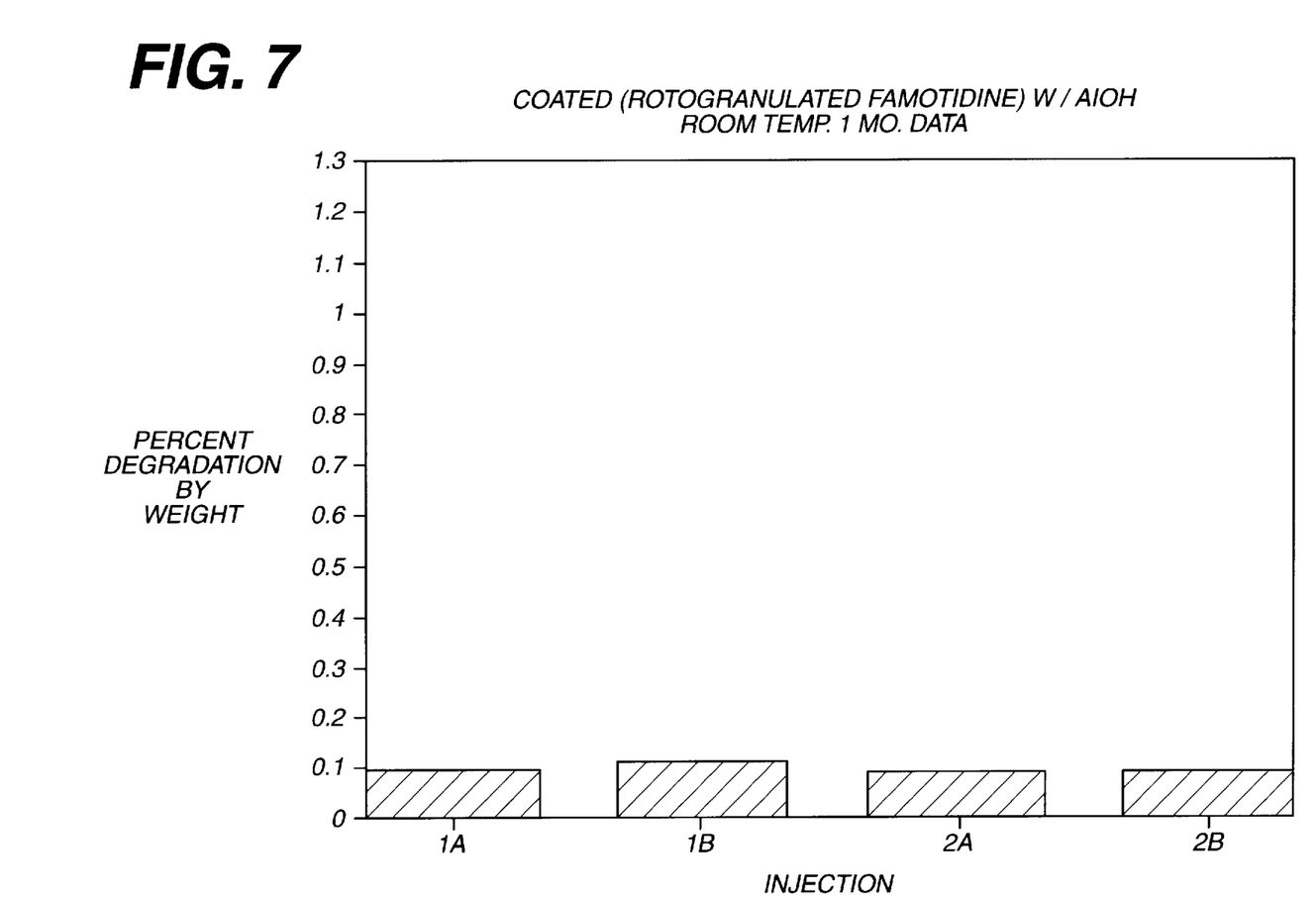
FIG. 7 provides a graphical presentation of the data from a stability test on an admixture of a powdered antacid (aluminum hydroxide) with a coated famotidine powder and a coated powdered famotidine. The data was obtained from two separate samples which were each injected twice into a column. This data evidences some enhanced stability for coated famotidine in the presence of a powdered antacid after being stored for one month at room temperature (as compared to the uncoated famotidine used in FIG. 5). The procedure used for the stability test is set forth in Example I.
Figure 8:
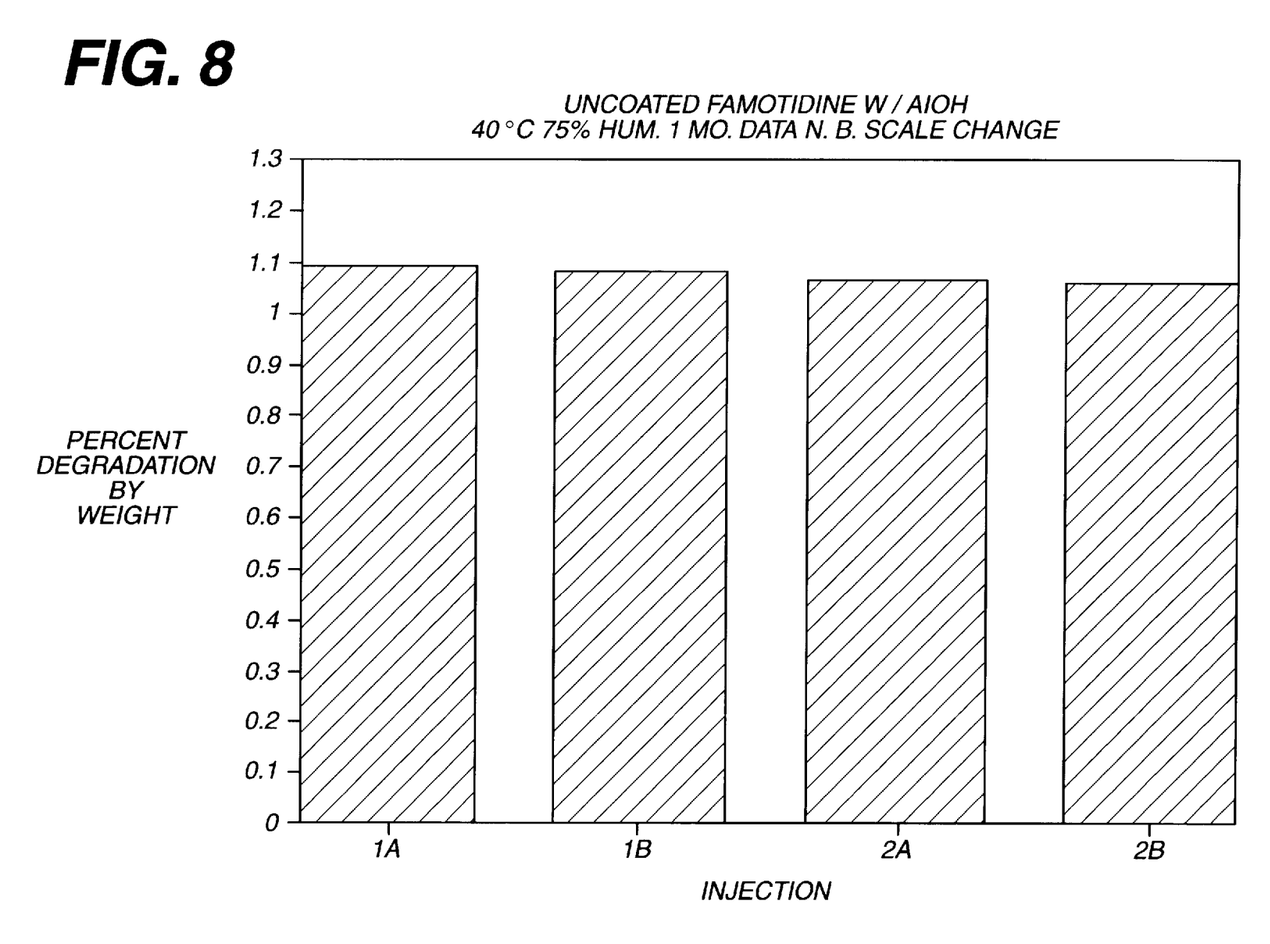
FIG. 8 provides a graphical presentation of the data from an accelerated stability test on an admixture of a powdered antacid (aluminum hydroxide) and powdered famotidine. The data was obtained from two separate samples which were each injected twice into a column. The data demonstrates the degradation of famotidine in the presence of an antacid after being stored for one month at 40° C. and 75% relative humidity. The procedure used for this stability test is set forth in Example I.
Figure 9:
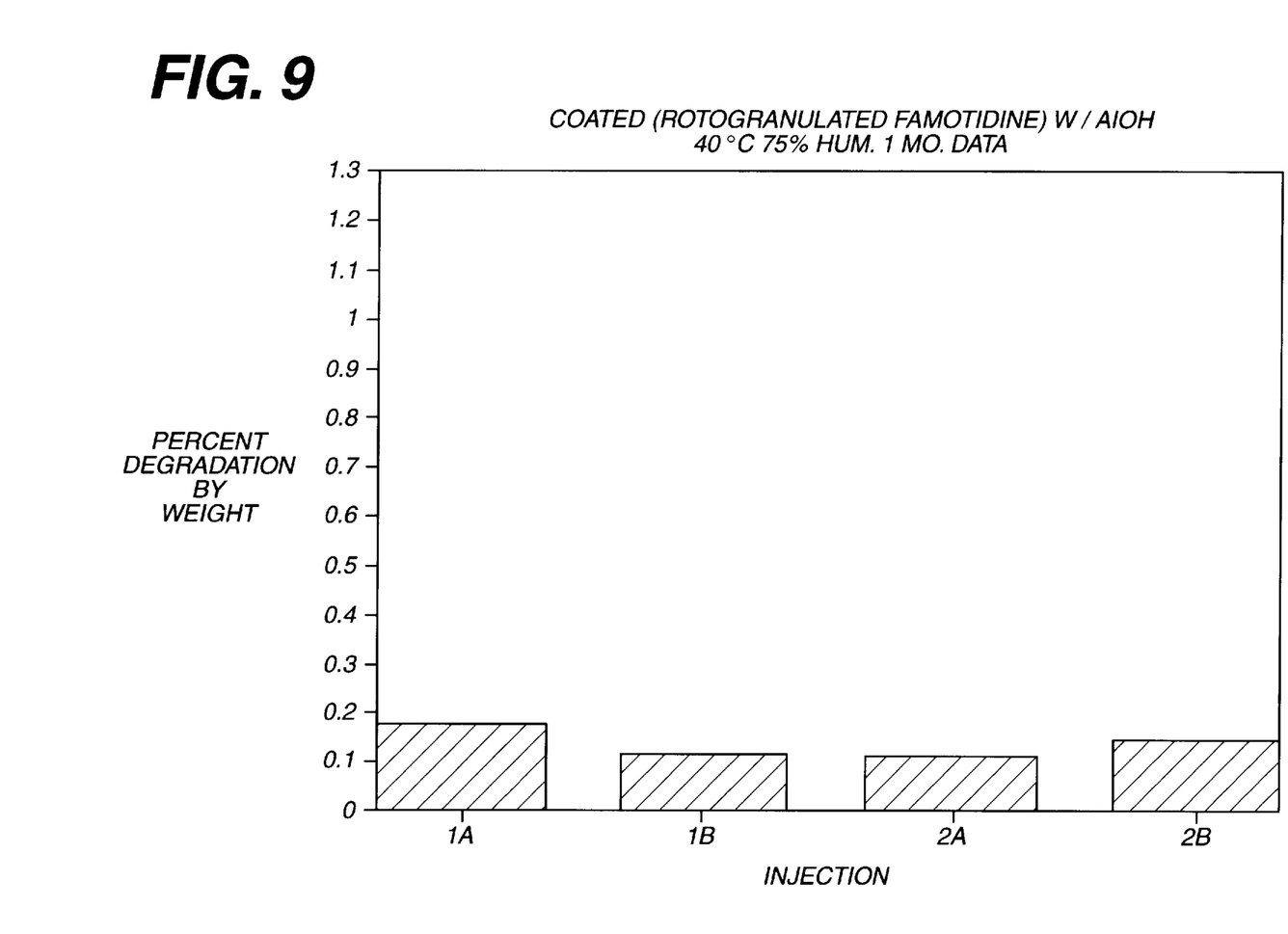
FIG. 9 provides a graphical presentation of the data from an accelerated stability test on an admixture of a powdered antacid (aluminum hydroxide) and a coated famotidine powder. The data was obtained from two separate samples which were each injected twice into a column. This data demonstrates the enhanced stability of a coated famotidine powder in the presence of a powdered antacid after being stored at 40° C. and 75% (as compared to the uncoated famotidine used in FIG. 7). The procedure used for this stability test is set forth in Example I.

FIG. 5 provides a graphical presentation of Famotidine with no antacid. FIG. 5 demonstrates that famotidine does not degrade significantly in the absence of an antacid. By comparison FIGS. 6 and 8 demonstrate that famotidine undergoes degradation in the presence of antacids both at room temperature and elevated temperature and humidity. However, FIG. 9 demonstrate that the use of a barrier compound significantly reduces the degradation of famotidine in the presence of an antacid during accelerated aging at 40° C. and 75% relative humidity.

EXAMPLE II

The Example provides a formulation for making a chewable tablet that contains coated famotidine granules admixed with granules of an antacid and formed into a solid oral dosage form. The weight provided hereinafter are based on a unit tablet weight for a 1080 mg tablet The granules of famotidine may be prepared by a rotary process wet granulation of Famotidine USP 10.0 mg, lactose NF 62.3 mg and hydroxypropyl methylcellulose 4.6 mg using purified water USP. The granules being produced by the wet granulation could then be roto-coated with a mixture of cellulose acetate 389-10 6.65 mg and hydroxypropyl cellulose 2.85 mg provided in a solution of acetone 80.0 mg and methanol 20.0 mg.

The tablets could then be made using the following ingredients:

| Antacid Blend | |
|---|---|
| Antacids (i.e. Calcium Carbonate) | 500.0 mg |
| Colloidal SiO$_2$ | 0.8 mg |
| (Peppermint) Flavor | 3.4 mg |
| Magnesium Stearate | 8.3 mg |
| Dextrates | 183.0 mg |
| Famotidine Blend | |
| Famotidine (Rotogranulated/Coated) | 87.97 mg |
| Mannitol | 257.80 mg |
| Microcrystalline Cellulose | 29.99 mg |
| Aspartame | 2.50 mg |
| Corn Starch | 1.23 mg |
| Mg. Stearate | 3.85 mg |
| Flavor (Peppermint) | 1.50 mg |
| Dye/Pigment | 0.12 mg |

Antacid Blend
 1. Place an antacids (i.e. calcium carbonate), Sorbitol NF, Peppermint flavor and magnesium stearate in a suitable sized P-K Twin Shell Blender. Blend for 5 minutes.
Famotidine Blend
 1. Screen Dye #2 through 60 mesh screen.
 2. Add Rotogranulated/Coated famotidine, mannitol, microcrystalline cellulose, aspartame, prosweet, magnesium stearate, Dye #2, P-K Blender. Blend for 5 minutes.
Tablet Compression
 1. Compressing the antacid blend at 2000–2500 PSI then famotidine blend is layered on top of antacid blend and compressed at 3000–3500 PSI into tablets to the following specifications on a Betapress rotary tablet machine equipped with the specified tooling:
 Punches: ⅝ inch×0.018, 0.002 Blended land,
 Flat Face Bevelled Edge (F.F.B.E.)
 Dies: ⅝ inch round
 Group Weight (10 tablets): Target—10.8 grams
 (Range: 10.3 grams–11.2 grams)
 Thickness: Target 5.5 mm (Range 5.25 to 5.75)
 Hardness: Target 4.5 kp (Range 3.2 to 5.9)
 Friability (%): 100 drops NMT 5.0%
 2. Collecting compressed tablets into a properly labelled container.

EXAMPLE III

This example provides a possible formulation for a chewable bilayer tablet. The weights provided hereinafter are based on a unit tablet weight for a 1080.58 mg bilayer tablet.

The granules of famotidine may be prepared by a rotary process wet granulation of Famotidine USP 10.0 mg, lactose NF 62 mg and hydroxypropyl methylcellulose 4.6 mg using purified water USP. The granules being produced by the wet granulation could then be roto-coated with a mixture of cellulose acetate 389-10 6.65 mg and hydroxypropyl cellulose 2.85 mg provided in a solution of acetone 82.30 mg and methanol 20.58 mg.

The bilayer tablets may then be made using the following ingredients:

| Antacid Blend | |
|---|---|
| Aluminum Hydroxide | 200 mg |
| Magnesium Hydroxide | 200 mg |
| Mannitol NF | 20 mg |
| Sorbitol NF | 20 mg |
| Peppermint Flavor | 3.4 mg |
| Dye #1 | 0.12 mg |
| Magnesium Stearate | 15 mg |
| Dextrates | 243.7 mg |
| Famotidine Layer | |
| Famotidine (Rotogranules coated to deliver 10 mg) | 87.97 mg |
| Mannitol NF | 257.8 mg |
| Peppermint Flavor | 1.60 mg |
| Microcrystalline Cellulose | 29.99 mg |
| Asparatame | 2.50 mg |
| Corn Starch | 1.23 mg |
| Magnesium Stearate | 3.85 mg |
| Dye/Pigment | 0.12 mg |

MANUFACTURING DIRECTIONS

Antacid Blend
 1. Place an antacid (such as calcium carbonate), Mannitol NF, Sorbitol NF, Peppermint flavor, Dye #1 and magnesium stearate in a suitably sized P-K Twin Shell Blender. Blend for 5 minutes.
Famotidine Blend
 1. Screen Dye #2 through 60 mesh screen.
 2. Add Rotogranulated/Coated Famotidine, Mannitol NF, Magnesium Stearate, Dye #2, P-K Blender. Blend for 5 minutes.
Tablet Compression
 1. Compressing one of the blends into a first layer then load the second blend into the press for final compression into a bilayer tablet to the following specifications on a Betapress rotary tablet machine equipped with the specified tooling:
 Punches: ⅝ inch×0.018, 0.002 Blended land,
 F.F.B.E.
 Dies: ⅝ inch round
 Group Weight (10 tablets): Target—10.8 grams
 (Range: 10.3–11.2 grams)
 Thickness: Target 5.5 mm (Range 5.25 to 5.75)
 Hardness: Target 4.5 (Range 3.2 to 5.9)
 Friability (%): 100 drops NMT 5.0%
 2. Collecting compressed tablets into a properly labelled container.

EXAMPLE IV

The Example provides a formulation for making a swallowable tablet that contains coated famotidine granules admixed with granules of an antacid and formed into a solid oral dosage form. The weight provided hereinafter are based on a unit tablet weight for a 1030 mg tablet.

The granules of famotidine may be prepared by a rotary process wet granulation of Famotidine USP 10.0 mg, Lactose NF 62 mg and hydroxypropyl methylcellulose 4.6 mg using purified water USP. The granules being produced by the wet granulation could then be roto-coated with a mixture of cellulose acetate 389-10 6.65 mg and hydroxypropyl cellulose 2.85 mg provided in a solution of acetone 82.30 mg and methanol 20.58 mg.

The tablets could then be made using the following ingredients:

| Antacid Blend | |
|---|---|
| Antacid i.e. Calcium Carbonate | 285.7 mg |
| Magnesium Hydroxide | 250.0 mg |
| Microcrystalline cellulose | 70.0 mg |
| Crosscarmellose sodium NF or Sodium Starch Glycolate NF | 40.0 mg |
| Famotidine Blend | |
| Famotidine (Rotogranules coated to deliver 10 mg) | 87.97 mg |
| Mannitol NF | 257.8 mg |
| Peppermint Flavor | 1.60 mg |
| Microcrystalline Cellulose | 29.99 mg |
| Asparatame | 2.50 mg |
| Corn Starch | 1.23 mg |
| Magnesium Stearate | 3.85 mg |
| Dye/Pigment | 0.12 mg |

MANUFACTURING DIRECTIONS

Antacid Blend

1. Place antacids (i.e. calcium carbonate and magnesium hydroxide), Microcrystalline cellulose and crosscarmellose (or sodium starch glycolate) sodium in a 16 quart P-K Twin Shell Blender. Blend for 2 minutes.

Famotidine Blend

1. Screen Dye #2 through 60 mesh screen.
2. Add Rotogranulated/Coated famotidine microcrystalline cellulose and magnesium stearate in a P-K Blender. Blend for 5 minutes.

Tablet Compression

1. Compressing the blend into caplets to the following specifications on a Betapress rotary tablet machine equipped with the specified tooling:

Punches: ⅝ inch×0.018, 0.002 Blended land, F.F.B.E.

Dies: ⅝ inch round

Group Weight (10 tablets): Target—10.3 grams (Range: 9.8 grams–10.6 grams)

Thickness: Target 5.0 mm (Range 4.9 to 5.15)

Hardness: Target 5.0 kp (Range 3.5 to 6.5 kp)

Friability (%): 100 drops NMT 5.0%

2. Collecting compressed tablets into a properly labelled container.
3. Coat with hydroxypropyl cellulose 26 mg film coat.
4. Print.

EXAMPLE V

The Example provides a formulation for making a swallowable tablet that contains coated famotidine granules admixed with granules of an antacid and formed into a solid oral dosage form. The weight provided hereinafter are based on a unit tablet weight for a 1030 tablet.

The granules of famotidine may be prepared by a rotary process wet granulation of Famotidine USP 10.0 mg, Lactose NF 62 mg and hydroxypropyl methylcellulose 4.6 mg using purified water USP. The granules being produced by the wet granulation could then be roto-coated with a mixture of cellulose acetate 389-10 6.65 mg and hydroxypropyl cellulose 2.85 mg provided in a solution of acetone 82.30 mg and methanol 20.58 mg.

The tablets could then be made using the following ingredients:

Components

| CaCO$_3$ | 257.00 mg |
|---|---|
| Acacia | 28.00 mg |
| Magnesium Carbonate | 251.00 mg |
| Microcrystalline Cellulose | 70.00 mg |
| Coated Famotidine Particles (coated particles prepared to deliver 10 mg of Famotidine) | 87.97 mg |
| Magnesium Stearate | 4.00 mg |
| Sodium Starch Glycolate NF or Cross Carmellose Sodium NF | 42.03 mg |

MANUFACTURING DIRECTIONS

1. Place all the components listed above in a suitably sized P-K Twin Shell Blender. Blend for 10 minutes.

Tablet Compression

1. Compressing the blend into caplets to the following specifications on a Carver Press at 4,000–4,500 PSI for 4 to 5 seconds equipped with the specified tooling:

Punches: 0.750 inch×0.075 inch×0.25 inch F.F.B.E.

Dies: 0.750 inch round

Group Weight (10 tablets): Target—10.3 grams (Range: 9.8 grams–10.6 grams)

Thickness: Target 5.0 mm (Range 4.9 to 5.15)

Hardness: Target 5.0 kp (Range 3.5 to 6.5 kp)

Friability (%): 100 drops NMT 5.0%

2. Collecting compressed tablets into a properly labelled container.
3. Coat with hydroxypropyl cellulose 26 mg film coat.
4. Print label.

Reasonable variations can be made in view of the disclosure above without departing from the spirit and scope of this invention.

I claim:

1. A solid oral dosage form for the treatment of gastrointestinal disorders comprising a therapeutically effective amount of impermeably coated famotidine granules for the treatment of gastric disorders and pharmacologically acceptable salts thereof; and a therapeutically effective amount of aluminum hydroxide or magnesium hydroxide wherein the oral dosage form has said coated famotidine granules and the aluminum hydroxide or magnesium hydroxide in contact with each other, but separated by said impermeable coating on the famotidine granules which is impermeable to the aluminum hydroxide or magnesium hydroxide.

2. The solid oral dosage form of claim 1 wherein the impermeable coating is a pharmaceutically acceptable film forming polymer selected from the group consisting of cellulose derivatives, polyvinyl pyrrolidone, polyvinyl alcohol, polyvinyl acetate, polyethylene glycols, copolymers of styrene and acrylate, copolymers of acrylic acid and methacrylic acid, copolymers of methacrylic acid and ethylacrylate, copolymers of methyl methacrylate and methacrylate, copolymers of acrylic acid and tertiary amino alkyl methacrylate, copolymers of methacrylate and tertiary amino alkyl methacrylate, copolymers of ethylacrylate methyl methacrylate and quaternary amino alkyl methacrylate and combinations of two or more thereof.

3. The solid oral dosage form of claim 2 wherein the amount of aluminum hydroxide or magnesium hydroxide is sufficient to provide from about 5 to about 20 ANC.

4. The solid oral dosage form of claim 1 wherein the impermeably coated granules contain:

| | |
|---|---|
| Famotidine USP | 8%–16% |
| Granulation Excipient | 76.5%–84% |
| coating | 8%–20% |

5. A method for manufacturing a solid oral dosage form comprising: a) forming granules containing famotidine for the treatment of gastric disorder; b) coating the granules with a coating impermeable to aluminum hydroxide or magnesium hydroxide to form impermeably coated famotidine granules; c) mixing a therapeutically effective amount of aluminum hydroxide or magnesium hydroxide with a therapeutically effective amount of impermeably coated famotidine granules and pharmaceutically acceptable excipients to form a compression mixture; then d) pressing the compression mixture to form a solid oral dosage form.

6. The method of claim 5 wherein the amount of aluminum hydroxide or magnesium hydroxide is sufficient to provide from about 5 to about 20 ANC.

7. The method of claim 6 wherein the impermeably coated granules contain:

| | |
|---|---|
| Famotidine USP | 8%–16% |
| Granulation Excipient | 76.5%–84% |
| Coating | 8%–20% |

* * * * *